United States Patent [19]
Mahaffey et al.

[11] 3,970,856
[45] July 20, 1976

[54] ULTRAVIOLET LIGHT APPLICATOR
[75] Inventors: James W. Mahaffey, Huntington, N.Y.; Charles J. Ziegler, Cleveland, Ohio
[73] Assignee: Cavitron Corporation, New York, N.Y.
[22] Filed: May 16, 1975
[21] Appl. No.: 578,284

[52] U.S. Cl. .............................. 250/493; 250/504
[51] Int. Cl.² .......................................... G01J 1/00
[58] Field of Search ............ 250/492, 493, 503, 504

[56] References Cited
UNITED STATES PATENTS

| | | |
|---|---|---|
| 2,538,685 | 1/1951 | Hansen ............................... 250/504 |
| 3,712,984 | 1/1973 | Lienhard ............................. 250/504 |
| 3,868,513 | 2/1975 | Gonser ................................ 250/504 |

Primary Examiner—Craig E. Church
Attorney, Agent, or Firm—Philip H. Pohl; Philip Sperber

[57] ABSTRACT

A handheld ultraviolet light applicator and power circuit for dental use is disclosed having a U-shaped argon filled glass ultraviolet lamp enclosed in a flat or curved lens and attached to a handle. Lamp excitation is supplied through a shielded cable from a power source having a high reactance transformer coupled to a fused safety circuit responsively cutting off power in the event of dangerous open circuit conditions.

13 Claims, 3 Drawing Figures

ULTRAVIOLET LIGHT APPLICATOR

BACKGROUND OF THE INVENTION

This invention relates to apparatus for radiating ultraviolet light. More particularly this invention relates to a novel ultraviolet light applicator device including a means for safely powering same.

In various dental procedures, it has been found desirable to apply to the surface of the teeth a polymeric sealing or adhesive material. For instance, certain types of polymeric material has been found to be effective as an adhesive for attaching various structures to the teeth as may be necessary in orthodonture or as a sealant for the tooth surface. The resins employed in such procedures are of a type which harden (cure) by being exposed to ultraviolet (UV) light. One such sealant or adhesive composition is described in U.S. Pat. No. 3,712,984 as the reaction product of bisphynel A and glycidyl methacrylate combined with about 20% benzoin methylether just before the resin is to be applied. To cure the resin it is then exposed to ultraviolet light for periods of up to 2 minutes depending on the extent and nature of the ultraviolet (UV) light supplied.

The aforesaid U.S. Pat. No. 3,712,984 issued Jan. 23, 1973, discloses apparatus apparently suitable for applying UV light in such procedures to harden and cure the adhesive in the patients mouth. As stated in the aforesaid patent, one specific requirement for a UV light applicator is the necessity of exposing the sealant to the light in the relatively confined area of the patient's mouth adjacent to the teeth. Of equal, if not greater importance, is the requirement that the patient not be exposed to any harmful effects by use of the UV light. Since it is known that certain ranges of frequency wavelengths of UV light are harmful to human tissue, minimal exposure, even to relatively safe UV wavelengths, is therefore, necessary. Secondly such light is necessarily generated by electrical apparatus which thereby also may generate excessive heat or present an electrical shock hazard to both the patient and the dentist. Finally such a UV light applicator should be small enough and convenient to use by the dentist and to fit inside the patient's mouth. As a practical matter, it must also be economical to purchase, maintain and use for this specific purpose.

As previously mentioned such an applicator is disclosed in the aforementioned U.S. Pat. No. 3,712,984 which shows a gunlike hand-held housing in which the UV light is generated and a bent tubular optical rod for transmitting and applying the UV light inside the patient's mouth. The apparatus shown in the aforesaid patent generates excessive heat including light in undesirable and dangerous frequencies of UV radiation. Therefore, the apparatus must be cooled, have a temperature sensitive cutoff switch, and a UV light filter in connection with its operation, all in the hand-held portion thereof. As such, the applicator disclosed in the aforementioned patent is quite complicated and cumbersome. Thus the filter is employed to eliminate undesirable UV short wavelength light under 320 nanometers (nm) as well as 90% wavelengths of the light in the 500 to 600 nm band. To provide for patient safety, the light transmitting quartz rod is employed to direct the filtered UV light to the desired area inside the patient's mouth. While such a device is presently in commercial use and is the only other such dental UV light applicator of which we are aware, it is quite clearly complicated and cumbersome together with other associated disadvantages. Another U.S. Pat. No. 3,868,513 issued Feb. 25, 1975 for a UV Radiation Projector is illustrative of another complex version of a UV applicator.

SUMMARY OF THE INVENTION

We have therefore invented an UV light applicator comprising a novel shaped light, including a power source and safety circuit having the following objects and advantages.

For instance, it is an object of this invention to provide a novel UV light able to be inserted in a confined area such as a patient's mouth;

Another object of this invention is to provide a UV light generating the preferred non-injurious long wavelength UV light as in the range of from about 315 nanometers into the infra red spectrum.

Still another object of the present invention is to provide a fail-safe UV light applicator.

Another object of the present invention is to provide a simple, effective power generating device for use in combination with the UV lamp and lens combination;

Yet another object of the present invention is to provide a safety circuit which automatically cuts off power to the device upon failure of the UV lamp or associated circuitry.

Another important object of this invention is to provide a novel curved UV lamp and applicator suitable for use in a patient's mouth;

Other objects and advantages of the present invention will become apparent from the summary of the invention which follows:

The UV applicator comprises in combination a argon filled fluorescent UV lamp, a high reactance transformer having its high voltage winding connected to the lamp, and an electrical power supply connected to the low voltage winding of the transformer. The UV lamp is a lime glass envelope having two electrodes at its end and filled with argon gas in the pressure range of at least 15 mm Hg and preferably between 24 and 30 mm Hg. The lamp is internally coated with a layer of strontium fluoroborate phosphor and binder composition and preferable two layers thereof. The UV lamp radiates ultraviolet (UV) light in the range of from about 310 nm (nanometers) to about 410 nm thereby clearly avoiding those UV wavelengths which are dangerous to living organisms and more particularly to a human patient and dentist. The applicator additionally comprises a safety circuit wherein a break in the lamp or its interconnecting cable, causing an open or no-load condition overloads a fuse cutting power. The fail-safe mode activates when current is cut off to a light emitting diode; a light sensitive resistor responds to generate a high current across a fuse in the main power line and blow the fuse.

The device briefly described above has the advantage of providing a small, low temperature UV lamp radiating UV light in the 310–410 nm range. This allows the lamp to be directly inserted into the patient's mouth. Secondly should this lamp or its interconnecting cable break thereby opening the load to the high voltage winding of the transformer, the safety circuit would immediately blow the main fuse. This is of major importance in such a medical and dental instrument.

With a view to further describing our invention, attention is directed to the brief description of the drawings and preferred embodiment which follow.

DESCRIPTION OF THE PREFERRED EMBODIMENTS

Figure 1:
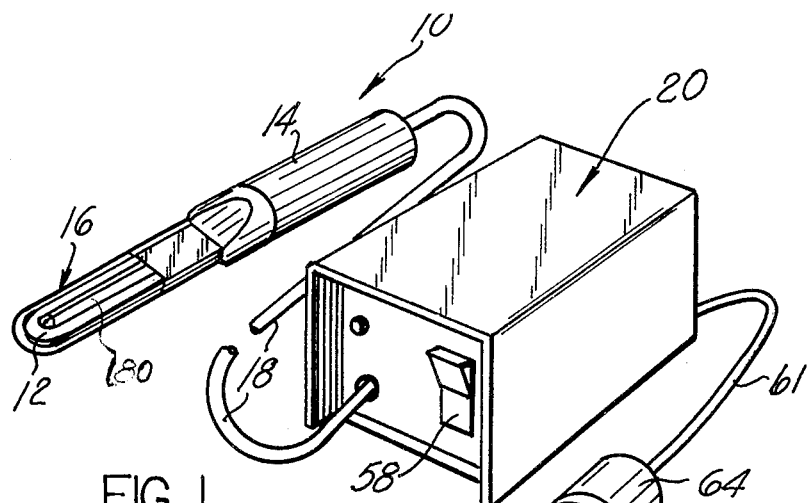
FIG. 1 of the drawings shows the ultraviolet applicator according to this invention.

As previously discussed in connection with the accepted use of various polymeric resins as adhesives and sealers by the dental profession we have invented a safe, effective, economical, and convenient applicator for generating ultraviolet radiation suitable to cure and harden such resins. The only example of a device that we are aware of for such use is that shown in U.S. Pat. No. 3,712,984 and previously described. Our device as shown in FIG. 1 of the drawings is a hand-held UV applicator 10 comprising a U-shaped ultraviolet lamp 12 attached to a tubular shaped handle 14 and enclosed in a transparent plastic lens cover 16. A coaxial interconnecting cable 18 connects the applicator 10 to a power supply or generator 20. The interconnecting cable 18 can be any desirable length as will be hereinafter described there being no functional reason for limiting the length thereof. The generator 20 is connected to any suitable source of conventional AC electrical current.

Figure 2:
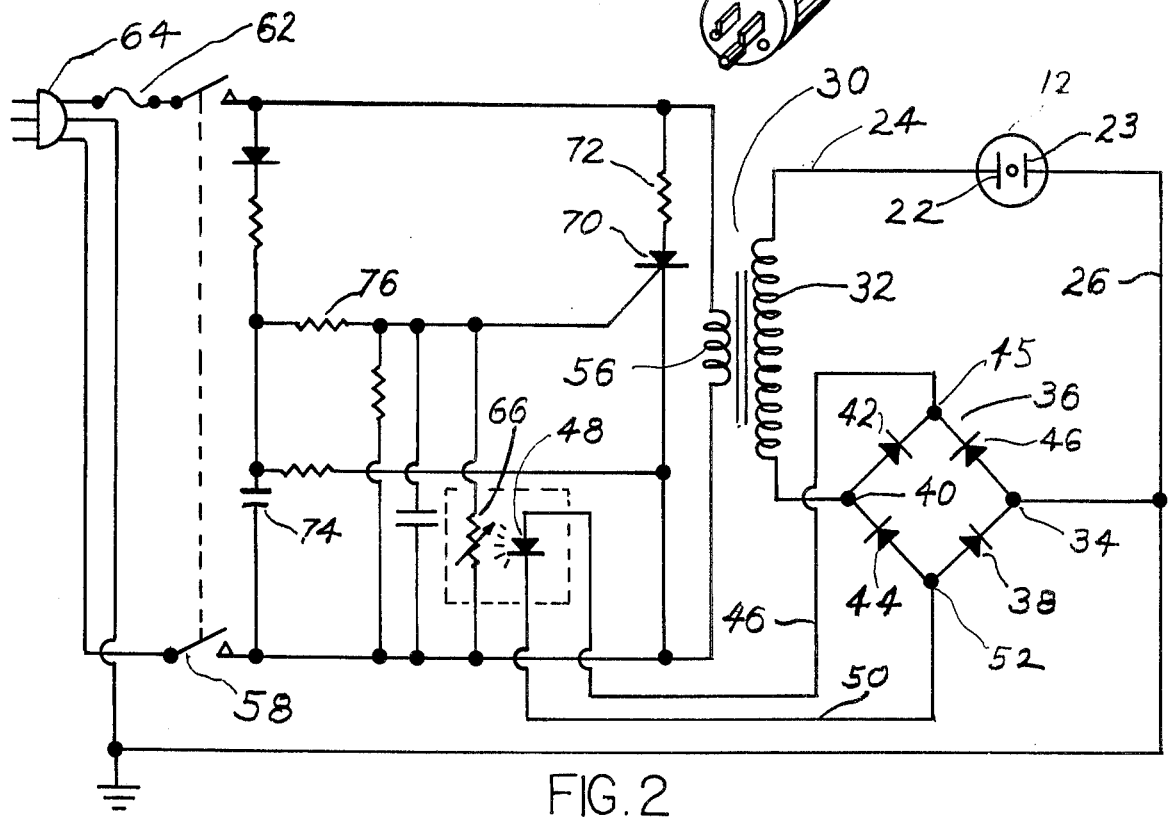
FIG. 2 is a schematic diagram of the UV light applicator electrical circuit.

With more particularity attention is now directed to the schematic shown in FIG. 2 of the drawings; where like reference numbers are used to identify similar elements. The ultraviolet lamp 12 is a U-shaped glass tube made from commercially available lime glass and preferably of relatively small diameter such as about ¼ inch. The light is internally coated with a strontium fluoroborate phosphor and is argon filled to a pressure of between about 24 mm and 30 mm Hg., after having been first evacuated. Lime glass it has been found is the only suitable glass for this apparatus allowing UV radiation in the 310–410 nm which is not dangerous to patient or user. Other glasses such as lead glass are opaque to UV radiation or to not filter out harmful UV radiation, i.e. quartz.

The strontium fluoroborate phosphor is applied to the internal surface of the lime glass tube by two applications of a liquid holding the material within the lamp tube being air dried to deposit the phosphor on the glass surface. The phosphor is bonded to the glass when the lamp is "burned in".

A minor amount of mercury metal is also deposited within the lamp glass envelope after evacuation. The phosphor is of the type which upon excitation fluorescence in the UV range with a peak wavelength of about 370 nm and a band width of from 350–400 nm. An example of a suitable phosphor is Type 2051 made by Sylvania Electric Products, Inc.

The lamp is sealed with two electrodes respectively 22 and 23 at each end respectively connected to the interconnecting cable 18 center lead 24 and shield 26. The interconnecting cable 18 is a commercially available coaxial one-conductor cable with an insulated shield and has been found to be particularly suitable for the high voltage, low amperage service required in this application.

The interconnecting cable is connected at its other end to the generator 20 in which a high reactance transformer 30 is mounted. The generator 20 contains the circuitry necessary to power the UV lamp in combination with the fail-safe features of this invention. The central lead 24 of the coaxial cable is connected to the high voltage winding 32 of the transformer 30 while the shielded lead 26 of the coaxial cable is connected within the box to one terminal 34 of a full wave rectifier circuit 36 having four diodes. The rectifier circuit is connected also to the chassis ground at terminal 34 thereby in effect providing grounding for the equipment. Terminal 40 in the rectifier circuit is connected to the input side of diode 42 and the output side of diode 44 in the rectifier circuit. The output side of diode 42 is in turn connected to circuit lead 46 which is connected to a light emitting diode 48. Terminal 45 is also connected to the output side of diode 46 which in turn is connected at its input side to terminal 34 and chassis ground. The other terminal of the light emitting diode 48 is connected through circuit lead 50 to terminal 52 of the rectifier circuit 36. Terminal 52 is in turn connected to the input side diode 44 and the input side of another diode 38 which latter diode is connected from its output side to terminal 34.

In operation the output of the high reactance transformer winding 32 powers the UV lamp through lead 24 and through its other connection to the rectifier circuit excites light emitting diode 48. As long as the high voltage winding of the high reactance transformer is loaded down by the UV light, the current passing from the transformer high voltage winding to the light emitting diode is sufficient to generate or cause the diode 48 to emit an effective quantity of light and the safety circuit inactive.

The high reactance transformer 30 is connected at its low voltage winding 56 to the terminals of a double pole double throw on/off switch 58. The on/off switch 58 is in turn connected at input terminals respectively to a power cord 61. A fuse 62 is connected to switch 58 and to the conventional power cord 61. Fuse 62 is connected to one of the "hot wires" of the power cord 61 which in turn is connected to a conventional grounded plug 64 suitable for insertion in any conventionally available socket. In operation therefore, when switch 58 is closed conventional house current is applied to the low voltage winding of 56 of the high reactance transformer 30 which in turn generates a very high voltage starting current for the UV lamp. In a short time, after a load is placed on the high voltage winding due to the UV lamp establishing a ionized circuit in its argon filled envelope between its two electrodes, the transformer power reduces to about 250 volts operating voltage needed to continually excite the UV lamp.

Should the interconnecting cable 18 or the UV lamp itself open, such would induce a high voltage potential across the open points. A fail-safe circuit means is employed in combination with the other circuit elements of this invention, portions of which have been previously described and referred to above. Therefore should the UV lamp 12 break or the interconnecting cable 18 become open the current passing through the rectifier circuit 36 would also cease to the light emitting diode 48, which, of course, would cease to radiate light. The light sensitive resistor would then rise appreciably in resistance (i.e. to 200,000 ohms from about 1000 ohms). The increased voltage now across the resistor, when reaching gate voltage of a silicon controlled rectifier 70, triggers it to pass sufficient increased current thru resistor 72 causing the fuse 62 to blow in less than ½ cycle of the line current. Finally, in order to prevent activation of the safety circuit when the apparatus is first turned on, a capacitance 74 and resistance 76 is incorporated in the circuit. This circuit is necessary since the lamp is in open-load condition at this time until the gas is ionized. The time constant of capacitance 74 and resistance 76 will therefore slowly charge to a direct current voltage of about 25 VDC and induce a positive bias in the gate of a silicon controlled rectifier 70 to prevent triggering. At start up, no light emanates from the light emitting diode because the lamp has still not ionized and resistance is therefore low. After the lamp starts the resistance across, the light sensitive resistor builds up in response to light from the light emitting diode. Both the light emitting diode and the light sensitive resistor are packaged together and sealed from ambiant light.

Figure 3:
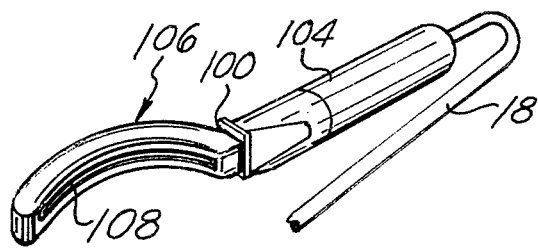
FIG. 3 shows a novel form of UV light applicator having a curved lamp and lens.

Referring now to FIG. 3 of the drawings, another novel form of a UV applicator 100 is shown. The applicator 100 is particularly adapted to be used in orthodonture and other dental procedures. Specifically, applicator 100 comprises a handle 104 identical to that used in applicator 10. A curved applicator lens 106 is connected to the handle 104 and encloses a curved, internally mounted U-shaped ultraviolet lamp 108. The lens 106 as well as that shown in FIG. 1 as lens 16 is made of non-UV stabilized polycarbonate or acrylic plastic and serves to allow transmittal of the UV radiation while being particularly resistant to breakage, deterioration and normal usage.

With particular reference to the curved applicator lens 106 and its enclosed lamp 108, the curve of the lens 106 conforms to one side of normal adult or child arch of teeth. This is a particularly valuable form of UV applicator as it allows uniform application of UV radiation over one side of the patient's mouth to cure the sealant or adhesive resin in the shortest patient exposure time. Not only is time important from an economic point of view, but the shortest exposure of patient and dentist to UV radiation is advantageous. The lamp is open on the inside of the curved lens 108 face as shown. Other than the curved shape of the lamp and lens combination, the various other elements of this version of the invention are similar to that described hereinbefore.

Also of importance is the mounting of a reflector 80 in back of the lamps 12 or 108 respectively which reflector 80 serves to increase the amount of ultraviolet radiation through the lens face. The reflector may be for instance a metalized Mylar material adhering to the inside surface of the lens or to a shaped backing between the lamp and the lens.

Having fully described our invention and wishing to cover those variations and modifications which would be apparent to those skilled in the art without departing from either the spirit or scope thereof.

We claim:
1. A ultraviolet light applicator comprising,
a handle,
lens means extending from said handle,
an ultraviolet lamp mounted in said lens means,
generator means connected to said ultraviolet lamp for starting and powering said lamp, and
safety circuit means for automatically shutting off power to said generator in response to failure of said lamp.

2. The applicator according to claim 1 wherein said lens is curved to conform to half the arch of teeth of a human mouth, said lamp also conforming to the shape of said lens whereby said lens, when inserted in the mouth opposite the arch of teeth, effectively irradiates the arch of teeth over the same time period.

3. The applicator according to claim 1 wherein said safety circuit means comprises
fuse means conductively connected between a source of conventional current and said generator,
a light emitting means electroconductively connected between said generator means and said lamp and emitting light in response to an electrical current between said generator and said lamp,
light responsive electrical power control means mounted adjacent said light emitting means for limiting electrical current in response to light from said emitting means, and appreciably and rapidly increasing electrical current in the absence of light from said emitting means, said control means being conductively connected to said fuse means whereby said increased electrical power being able to cause said fuse means to blow and open the connection between said conventional current source and said generator.

4. The applicator of claim 1 wherein said lamp comprises a sealed lime glass envelope filled with argon gas to a pressure of at least 15 mm Hg.,
a layer of phosphor internally coating said glass envelope, and
two electrodes mounted in said envelope at a spaced apart distance from each other and externally conductively connected to said generator means.

5. The applicator according to claim 4 wherein
said glass envelope is a U-shape tube having one of said electrodes internally mounted at each end of said lamp,
said layer of phosphor being a composition comprising strontium fluoroborate fluorescing in the ultraviolet band between about 350 nm and 400 nm, and
said tube is filled with said argon to a pressure between about 24 and 30 mm Hg.

6. The applicator according to claim 4 wherein said lens comprises a non-ultraviolet stabilized plastic selected from group consisting of polycarbonate and acrylic plastics.

7. The applicator according to claim 1 where said generator means comprises
a high reactance transformer having a low voltage winding connected to a source of conventional electrical current, and a high voltage winding connected to said lamp whereby said transformer provides sufficiently high voltage to start said lamp and reduces to a lower sustaining voltage to maintain said lamp in an energized condition.

8. The applicator according to claim 7 wherein said generator transformer is connected to said lamp by a single lead coaxial cable.

9. The applicator according to claim 7 wherein said safety circuit means comprises
fuse means conductively connected between a source of conventional current and said generator,
a light emitting means electroconductively connected between said generator means and said lamp and emitting light in response to an electrical current between said generator and said lamp, light responsive electrical power control means mounted adjacent said light emitting means for limiting electrical current in response to light from said emitting means, and appreciably and rapidly increasing electrical current in the absence of light from said emitting means, said control means being conductively connected to said fuse means whereby said increased electrical power being able to cause said fuse means to blow and open the connection between said conventional current source and said generator.

10. The applicator according to claim 9 wherein said safety circuit additionally comprises time delay means for delaying actvation for a limited time period of said light responsive electrical power control means until said lamp has been energized thereby providing current to said light emitting means.

11. The applicator of claim 10 wherein said light emitting means is a light emitting diode, said light responsive control means is a light sensitive resistor, said time delay means is a capacitance-resistance circuit characterized by a time delay impedence, said safety circuit means additionally comprising a rectifier circuit for transmitting current to energize said light emitting diode from said lamp, and silicon controlled rectifier means connected at its gate to said time delay means and to said light responsive resistor for triggering said gate and passing sufficient power through said silicon controlled rectifier means to blow said fuse.

12. A method of treating the arch of teeth located in a patient's mouth, said method comprising inserting a lens enclosing a means for radiating ultraviolet light in the patient's mouth opposite the arch of teeth, said lens being curved to conform with the shape of a normal human arch of teeth, and energizing said lamp for a sufficient period to irradiate the arch of teeth opposite the lens with a sufficient amount of ultraviolet light.

13. The method of claim 12 additionally comprising the step of initially coating the teeth with a resin composition which cures rapidly upon exposure to ultraviolet light.

* * * * *